US009664658B2

(12) United States Patent
Roberts et al.

(10) Patent No.: US 9,664,658 B2
(45) Date of Patent: May 30, 2017

(54) METHOD, DEVICE, AND SYSTEM FOR AEROSOL DETECTION OF CHEMICAL AND BIOLOGICAL THREATS

(71) Applicant: SRC, Inc., North Syracuse, NY (US)

(72) Inventors: Marc P. Roberts, Alexandria, VA (US); Stephen R. Houghton, Tully, NY (US)

(73) Assignee: SRC, INC., North Syracuse, NY (US)

( * ) Notice: Subject to any disclaimer, the term of this patent is extended or adjusted under 35 U.S.C. 154(b) by 250 days.

(21) Appl. No.: 14/595,760

(22) Filed: Jan. 13, 2015

(65) Prior Publication Data

US 2016/0202222 A1 Jul. 14, 2016

(51) Int. Cl.
| | | |
|---|---|---|
| G01N 33/00 | (2006.01) | |
| G01N 33/497 | (2006.01) | |
| G01N 21/65 | (2006.01) | |
| G01N 1/22 | (2006.01) | |

(52) U.S. Cl.
CPC ....... *G01N 33/0004* (2013.01); *G01N 1/2202* (2013.01); *G01N 21/65* (2013.01); *G01N 33/497* (2013.01); *G01N 33/0057* (2013.01); *G01N 2033/4975* (2013.01)

(58) Field of Classification Search
CPC ... G01N 2001/2223; G01N 2033/4975; G01N 21/65; G01N 33/0004; G01N 33/0057; G01N 33/497
See application file for complete search history.

(56) References Cited

U.S. PATENT DOCUMENTS

| 5,175,433 A | 12/1992 | Browner et al. |
| 5,866,430 A | 2/1999 | Grow |
| 6,750,449 B2 | 6/2004 | Marcus |
| 7,057,721 B2 | 6/2006 | Gardner, Jr. et al. |
| 7,170,052 B2 | 1/2007 | Furutani et al. |
| 7,333,190 B1 | 2/2008 | Pendell-Jones et al. |
| 7,391,557 B1 | 6/2008 | Bruch et al. |
| 7,436,515 B2 | 10/2008 | Kaye et al. |

(Continued)

FOREIGN PATENT DOCUMENTS

| JP | 2007171012 | 7/2007 |
| WO | 2008036710 | 3/2008 |

OTHER PUBLICATIONS

Steiner et al., "Detection of a Chemical Warfare Agent Simulant in Various Aerosol Matrixes by Ion Mobility Time-of-Flight Mass Spectrometry". Analytical Chemistry, [Online] vol. 77, No. 15, Aug. 1, 2005, pp. 4792-4799.

(Continued)

*Primary Examiner* — Francis Gray
(74) *Attorney, Agent, or Firm* — Bond Schoeneck & King, PLLC; Blaine Bettinger; George McGuire (57) ABSTRACT

Methods and systems for identifying an aerosolized agent. A method for identifying an aerosolized agent includes the steps of providing a sample potentially containing an aerosolized agent, concentrating the sample with an aerosol collector, analyzing the concentrated sample on a collection substrate using spectroscopy to produce an aerosolized agent analysis output, comparing the analysis output to a database of known agent analysis outputs; identifying the aerosolized agent based on the comparison; and alerting a user to the presence of an aerosolized agent in the sample.

17 Claims, 11 Drawing Sheets

(56) References Cited

U.S. PATENT DOCUMENTS

| | | | |
|---|---|---|---|
| 7,450,227 B2 | 11/2008 | Dwight et al. | |
| 7,511,809 B2* | 3/2009 | Schneider | G01N 1/2273 |
| | | | 356/301 |
| 7,532,320 B2* | 5/2009 | Neiss | G01J 3/02 |
| | | | 356/301 |
| 7,636,154 B1 | 12/2009 | LaValley et al. | |
| 7,687,276 B2 | 3/2010 | Kunz | |
| 7,993,585 B2 | 8/2011 | Black et al. | |
| 7,999,928 B2 | 8/2011 | Beckstead et al. | |
| 8,071,938 B2 | 12/2011 | Guharay | |
| 8,093,065 B2 | 1/2012 | Poponin | |
| 8,134,122 B2 | 3/2012 | Guharay | |
| 2005/0230615 A1* | 10/2005 | Furutani | B82Y 10/00 |
| | | | 250/287 |
| 2005/0263694 A1* | 12/2005 | Hayek | H01J 49/0036 |
| | | | 250/287 |
| 2008/0302666 A1 | 12/2008 | Benner et al. | |
| 2010/0040979 A1 | 2/2010 | Weimer | |
| 2010/0079753 A1 | 4/2010 | Hehlen | |
| 2010/0296086 A1 | 11/2010 | Wang et al. | |
| 2011/0045517 A1* | 2/2011 | Derringer | C12Q 1/46 |
| | | | 435/20 |
| 2011/0127421 A1* | 6/2011 | Finlay | G01N 30/72 |
| | | | 250/283 |
| 2012/0038908 A1 | 2/2012 | Beckstead et al. | |
| 2012/0040330 A1 | 2/2012 | Carpenter | |

OTHER PUBLICATIONS

Martin, "The Application of Single Particle Aerosol Mass Spectrometry for the Detection and Identification of High Explosives and Chemical Warfare Agents". Lawrence Livermore National Laboratory [Online], Nov. 28, 2006, pp. 8-16, 18-21.

Sferopoulos, "A Review of Chemical Warfare Agent (CWA) Detector Technologies and Commercial-Off-The-Shelf Items". Human Protection and Performance Division Defence Science and Technology Organisation [Online], Mar. 2009, pp. 16-31, 52-56.

ChemPro100i, https://www.rkb.us/contentdetail.cfm!content_id=202185&overridesubt%ED%AF%80%ED%B1%9 (accessed Mar. 21, 2012), pp. 1-3.

* cited by examiner

110 Provide an air sample potentially comprising an aerosol

120 Collect the sample with an aerosol collector

130 Analyze collected aerosol particles with spectrometer

140 Identify collected aerosol particles

150 Send alert to user

160 Analysis of sample by supporting labs

METHOD, DEVICE, AND SYSTEM FOR AEROSOL DETECTION OF CHEMICAL AND BIOLOGICAL THREATS

FIELD OF THE INVENTION

The present invention relates to a device, method, and system for detecting a chemical warfare agent, toxic industrial chemical, explosive, or other chemical threat in the aerosolized form, and more specifically a concentrating collection device, spectroscopic signal enhancing technique, and sensor-fused system capable of detecting a chemical threat aerosol in a field-deployed setting autonomously and in near real-time.

BACKGROUND

There is an increasing demand for methods and systems capable of detection, quantitative characterization, and notification of the presence of chemical, biological, radiological, nuclear, and/or explosive ("CBRNE") hazards across a broad range of disciplines, including defense, food safety, homeland security, and medical diagnostics, among many others. While there is existing technology for the detection and quantitative identification of chemical and biological hazards, these sensors are generally large, bulky, and/or slow sensor systems that require considerable time and effort to utilize or to move from one location to another. Accordingly, there is a continued need for fast, efficient, and portable sensor systems for hazard detection, as well as for systems that subsequently notify a user of any hazard that is detected.

A chemical attack can include threat chemicals released as an aerosol dispersion. In such an attack, the aerosol dispersion could be composed of threat chemicals in the form of any combination of solid particles, liquid droplets, or vapors. Many CBRNE chemical detectors do not easily collect, concentrate, and analyze chemical threats in all states of matter.

One method used for the identification of biological or chemical threats is Raman spectroscopy. Raman is a form of vibrational spectroscopy proven to exhibit excellent selectivity for the purpose of material identification and has been the handheld liquid/solid analyzer of choice for defense and homeland security applications. Raman spectroscopy utilizes a monochromatic laser to interrogate unknown samples. Depending on the specific wavelength of light, the composition of the background material, and properties of the chemical being interrogated, the light can result in absorption, transmission, reflection, or scattering. Light that is scattered from the sample can result in either elastic collisions resulting in Raleigh scattering or inelastic collisions resulting in Raman scattering. Raman light scattering is the result of a photon exciting the molecule through vibration and rotation of its bonds from a ground state to a virtual energy state. Once the molecule relaxes, it emits a photon and returns to a rotational or vibrational state different from the original ground state. The energy delta between these levels results in a shift of the emitted photon's frequency away from the excitation wavelength. The result is a detection method based on the peak intensities at characteristic shifts measured in wavenumber (cm-1) or wavelength (nm) and attributed to specific molecules, thus generating a Raman spectral "fingerprint" by recording the intensity of light as a function of the energy difference between the laser and Raman scattered light. This output is reproducible and allows development of identification algorithms for the spectral fingerprints. However, Raman detectors are not equipped or configured to collect, detect, or analyze a released aerosol.

One difficulty with fielded Raman detectors is that some background surfaces undergo a competing phenomenon, referred to as fluorescence, which can mask the signal of the analyte. For example, plastics and surfaces with organic binders, paints, and adhesives can obscure a Raman signal and affect the sensitivity of analysis. Modulation of the wavelength of the incident light can alleviate some fluorescence effects, but most fielded instruments operate at a static incident laser wavelength chosen to balance these effects as well as to conserve power, weight, and complexity of the device. Since reducing fluorescence of the sample is not possible at a static wavelength, our invention drastically reduces the interfering background fluorescence and amplifies the analyte signal by providing an ideal collection substrate for and analysis by spectroscopy.

Detection level of this invention as it pertains to a dry chemical aerosols such as acetaminophen have resulted in positive detection and identifications of aerosol clouds down to concentrations of 0.001-0.005 $mg/m^3$ when collected and concentrated over 5 minutes using the device described herein. Detection of chemical aerosol clouds at a concentration of 0.0005 $mg/m^3$ have been achieved following 10 minute collections. Detection levels of liquid droplets of 0.1 µL (100 nanoliters) has been shown to be rapid with the system described herein.

Accordingly, there is a continued need for methods and systems that use Raman spectroscopy to analyze an aerosol.

SUMMARY OF THE INVENTION

The present disclosure is directed to a device, method, and system for analyzing an aerosol in order to identify a biological or chemical threat within that aerosol in near real-time in the field. The invention comprises an aerosol collection substrate that has a high particle collection and retention efficiency, concentrates aerosolized samples, reduces or eliminates background fluorescence, and ultimately amplifies the Raman signal for the corresponding detector. Configuration of the aerosol inlet to focus collected material at the point of analysis by the spectroscopic detector is also a critical design feature. This collector is designed such that the aerosol is concentrated by impaction, accretion, filtration, or absorption.

The present disclosure is also directed to a device, method, and system with an integrated trigger system to initiate sample collection upon detection of a chemical and biological threat. This trigger system can include algorithms to differentiate between biological and chemical threats. Such a trigger may be a modified UV light induced fluorescence ("LIF") or Raman Scattering detector using either a laser, light emitting diode ("LED"), or other appropriate excitation sources.

In particular, the disclosure provides a mechanism for integrating Raman spectroscopy with a dry aerosol collector in order to collect, concentrate, and identify biological or chemical threats within that aerosol. Integration of Raman spectroscopy with an aerosol collector presents a significant advantage in that this analytical technique is non-destructive and permits transfer and additional examination of collected sample at supporting labs with other instrumentation. In addition, the extraction of the collected chemical or biological threats can be accomplished with a replaceable collection and extraction cup.

Furthermore, the invention can collect, concentrate, detect, and identify organic vapors. The aerosol collector inlet design and aerosol collection substrate will collect organic chemical vapors sampled by the system. The organic vapors will be absorbed into the aerosol collection substrate for detection and identification by the integrated Raman spectroscope.

Additionally, according to an embodiment, the invention can collect, concentrate, detect, and identify an aerosolized agent in the vapor, liquid aerosol, and/or solid aerosol state of matter.

Lastly, according to an embodiment of the method, the lowest achievable level of detection attained by this integrated system is identifying an aerosol cloud of concentration 0.001 mg/m$^3$ following a 5 minute collection which exceeds the current capabilities of may deployed CBRNE detection systems.

In accordance with the foregoing objects and advantages, a method for identifying an aerosolized agent is provided. The method includes the steps of: (i) providing a sample, the sample potentially containing an aerosolized agent; (ii) concentrating the sample with an aerosol collector, the aerosol collector comprising a collection substrate; (iii) analyzing the concentrated sample on the collection substrate using spectroscopy to produce an aerosolized agent analysis output; (iv) comparing the analysis output to a database comprising a plurality of known agent analysis outputs; (v) identifying the aerosolized agent based on said comparing step; and (vi) alerting a user to the presence of an aerosolized agent in said sample.

According to an embodiment, the agent is a biological and/or chemical agent.

According to an embodiment, the aerosolized agent exists in the vapor, liquid aerosol, and/or solid aerosol state of matter.

According to an embodiment, the method includes the step of transferring the collected sample to supporting laboratory for further analysis.

According to an embodiment, the method includes the step of triggering the concentration of the sample by aerosol collector.

According to an embodiment, the method includes the step of analyzing the concentrated sample using a second sensor. According to an embodiment, the second sensor is selected from the group consisting of an IMS, PID, FTIR, GC-MS, and combinations thereof, among other sensors.

According to a second aspect is a device configured to concentrate an aerosolized agent. The device can include: (i) an air movement device configured to force air comprising the aerosol into an inlet, wherein said air may comprise the aerosolized agent; (ii) a collection chamber configured to direct the air to a collection substrate; (iii) a spectrometer probe positioned to analyze a surface of the collection substrate.

According to an embodiment, the aerosolized agent is a biological and/or chemical agent.

According to an embodiment, the aerosolized agent exists in the vapor, liquid aerosol, and/or solid aerosol state of matter.

According to an embodiment, the air movement device is a fan.

According to an embodiment, the collection substrate is replaceable, and is configured to limit interference by background fluorescence.

According to a third aspect is a system to identify an aerosolized agent, the system including: (i) an aerosol collector configured to concentrate an aerosolized agent; (ii) a spectrometer in communication with the aerosol collector, the spectrometer configured to analyze the concentrated aerosolized agent; (iii) a database of biological and chemical agents; and (iv) a processor in communication with the spectrometer and the database, the processor configured to compare the results of the analysis to the database of known agents, and further configured to identify the concentrated aerosolized agent based on the comparison.

According to an embodiment, the aerosolized agent is a biological and/or chemical agent.

According to an embodiment, the aerosolized agent exists in the vapor, liquid aerosol, and/or solid aerosol state of matter.

According to an embodiment, the system includes a trigger for initiating aerosol collection by the aerosol collector.

According to an embodiment, the system includes an auxiliary sensor in communication with the trigger. The sensor may be, for example, selected from the group consisting of IMS, PID, FTIR, GC-MS, and combinations thereof, among other sensors.

According to an embodiment, the system includes a user interface.

These and other aspects of the invention will be apparent from reference to the embodiments described hereinafter.

BRIEF DESCRIPTION OF THE DRAWINGS

The present invention will be more fully understood and appreciated by reading the following Detailed Description in conjunction with the accompanying drawings, in which.

DETAILED DESCRIPTION

According to an embodiment is a device, method, and system for collecting, concentrating, detecting, and identifying an aerosolized chemical/biological warfare agent or threat chemical. According to one embodiment is a collection/detection system capable of detecting a chemical threat aerosol in near-real-time while allowing for subsequent analysis of the aerosol by a supporting laboratory to confirm the presence of a chemical threat. According to another embodiment is the integration of chemical aerosol detection capability with a detector system used to detect and collect biological aerosols in a manner that allows the integrated system to detect both chemical and biological threat aerosols. Addition of a near-real-time ion mobility spectrometry ("IMS") based chemical vapor detector to the integrated chemical and biological aerosol detector system results in a detector system capable of detecting most chemical and biological threats to include chemical aerosols, biological aerosols, and chemical vapors. In such an integrated detector system, the Raman-based chemical aerosol detector component can be used to augment the capabilities of the IMS detector, which reduces the likelihood of false positive alarms generated by the IMS detector. Indeed, a well-characterized and widely recognized disadvantage of IMS-based field chemical detectors is the high frequency of false positives due to its dependency on molecular weight of a substance.

Therefore, according to an embodiment is the integration of a Raman spectrometer and dry aerosol collector with an IMS-based chemical vapor detector to augment and enhance the selectivity of the IMS detector. The incorporation of Raman spectroscopy with aerosol collection, including for example a dry aerosol sampler, allows for near-real-time identification of a chemical threat aerosol. This embodiment also allows for confirmatory analysis of the collection substrate by a supporting laboratory to verify the release of a chemical threat aerosol and/or allows for more precise analysis of the aerosol's composition. According to one embodiment, following an alarm noting a possible release of a chemical threat aerosol, a user can collect the contaminated collection substrate from the aerosol collector and process the sample at a supporting laboratory. Spectroscopic detection methods are not expected to degrade most known chemical threat compounds, and should not interfere with later analysis by a supporting laboratory.

Figure 1:
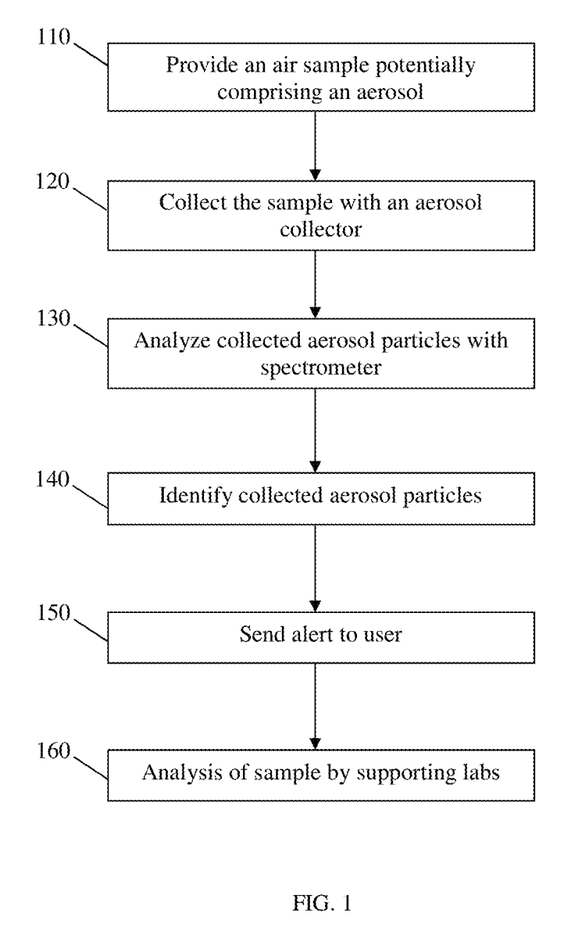
FIG. 1 is a flowchart of a method of collecting and detecting a biological and/or chemical agent or aerosol according to one embodiment.

An embodiment of a method for concentration and identification is depicted in FIG. 1, which starts at step 110 with a sample of any volume of ambient air potentially comprising an aerosol threat. The aerosol can be any aerosol, and can comprise an aerosolized biological or chemical agent. The unknown aerosolized biological or chemical agent can be any biological or chemical agent of interest, including those used as a biological or chemical weapon. Aerosolized chemical agents may be in the form of thickened or unthickened liquid droplets, solid particulates, or vapors. Agents of biological origin include but are not limited to numerous bacterium, virus, prion, and fungus varieties, as well as biological toxins. Some examples of prime targets for detection by the present system include microorganisms such as *Bacillus anthracis* spores, members of the genii *Burkholderia, Rickettsia, Shigella, Vibrio,* and *Yersinia pestis,* viruses such as the smallpox virus, and toxic proteins such as ricin (from *Ricinus communis*) and botulinum toxin (from *Clostridum botulinum*), among many other possible aerosolized biological agents. Examples of some targeted chemical agents of interest include sulfur/nitrogen mustard, VX nerve agent, soman, tabun, and sarin, among many other toxic industrial chemicals. In addition, precursors, intermediates, degradation products, residual impurities/media, or known components of chemical and biological weaponization can be readily detected given their addition to the Raman spectral library.

Figure 2:
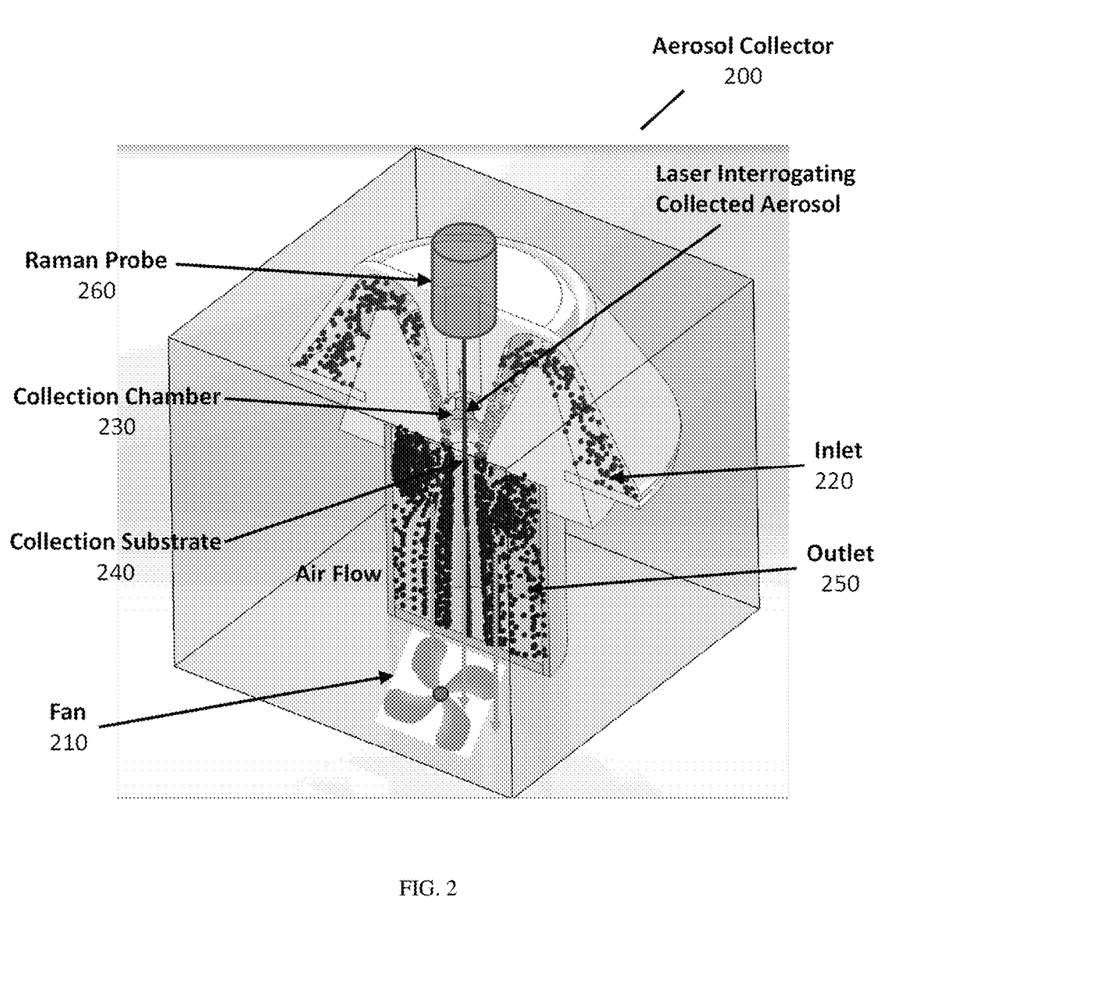
FIG. 2 is a schematic representation of a device adapted to collect and detect a biological and/or chemical agent or aerosol according to one embodiment.

At step 120, an aerosol collector or dry particulate sampler system collects the aerosol. Referring to FIG. 2, according to an embodiment, is an aerosol collector 200. Although aerosol collector 200 is depicted as a box-like structure in FIG. 2, the device can be any size, shape, or configuration. Accordingly, aerosol collector 200 can be utilized in a wide variety of locations. The collector design used may be a function of the type of aerosol, targeted particle size, chemical/biological properties, desired sensor sensitivity and frequency of use. Therefore, variations in collector designs may range in function from a filter holder cassette, inertial classifier such as a body impactor, conventional impactor, virtual impactor, cyclone impactor, jet-in-well impactor, to an electrostatic precipitator. Any combination of techniques thereof is also possible to maximize collection efficiency of the aerosol threat. The inlet however, may be designed to attain particle focusing and/or separating if desired. To attain alignment of collected aerosol with analysis point on the collection substrate may have designs encompassing features such as a laminar focusing and acceleration jet, cyclone or conical nozzle, sampling cowl, insect and precipitation screen/cover.

Figure 4:
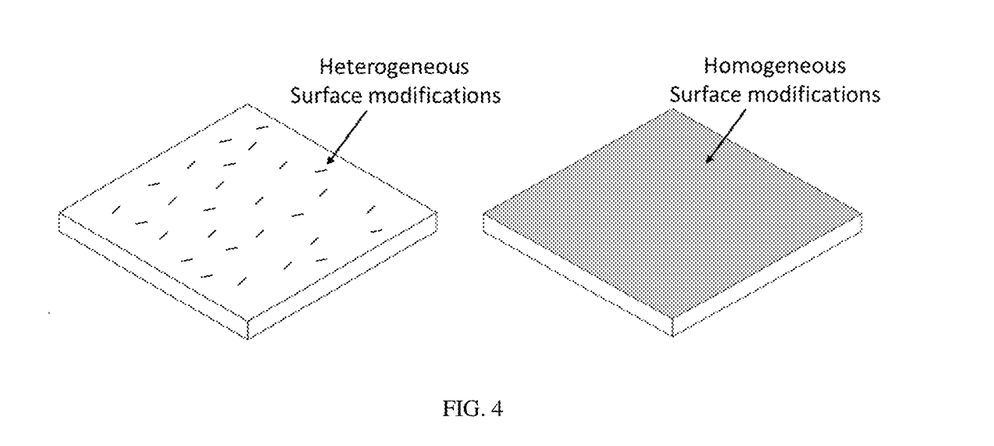
FIG. 4 is a representation of both heterogeneous and homogeneous Raman enhancing, fluorescence suppressing collection substrate according to one embodiment.
Figure 5:
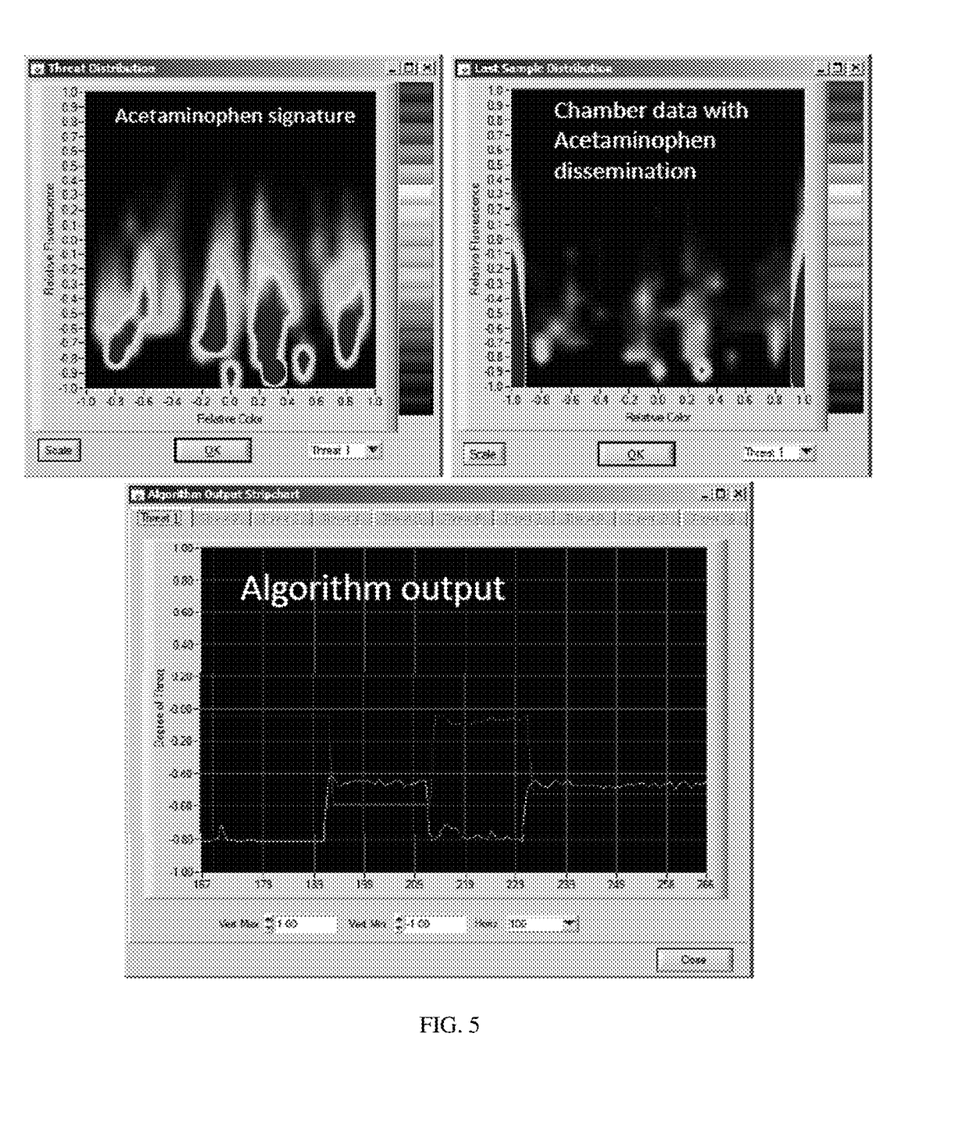
FIG. 5 is a representative fluorescence spectral signature obtained by a trained LIF sensor detecting an aerosol dissemination of acetaminophen.

According to an embodiment, the aerosol collector is designed to capture airborne biological and/or chemical aerosol particles onto a collection substrate using a fan, blower, or pump generating airflow of a specific volumetric flow rate directed at or through the collection substrate. Accordingly, aerosol collector 200 includes a fan, blower, pump, or other device 210 to push or pull air, possibly containing the aerosolized agent, through an inlet 220 into a collection chamber 230. The collector can be designed to filter, impact, intercept, suspend, absorb, or electrically precipitate aerosolized threats out of a sampled volume of air. For example, inside collection chamber 230 there can be situated an aerosol collection substrate 240 that collects, filters, intercepts, absorbs, and/or electrically precipitates the aerosolized agent from the sampled volume of air. For example, as shown in FIG. 2, the air is forced through aerosol collection substrate 240. The aerosol collection substrate that interfaces with the device may be comprised of one or multiple features that include materials that are derivative of oxides of metaloids, or metals. Appropriate collection substrate could be a porous, fibrous aerosol sampling material such as those typically used in filters, thimbles, or cartridges. Polymeric membranes, such as cellulose, or those composed of organic binders and inorganic woven fibers, may also be suitable for the collector. In addition, a suitable nonpermeable surface such as an impaction plates, liquid collection trap, well, cup, or impinger. The collection substrate could be homogeneous metal or alloy with or without uniform repeating chemical functionalization. Alternatively, a suitable heterogeneous material with Surface Enhanced Raman Spectroscopy ("SERS") or surface enhanced resonance Raman scattering ("SERRS") attributes such as metallic nanoparticle decorated filter paper, membrane, or sol-gel is feasible. Alternatively, homogeneous, nanostructured, or uniformly functionalized substrates are possible to attain an amplified spectroscopic signal. The surface could also be integrated or functionalized with bio-receptors (e.g. biomarkers, antibodies or molecular conjugates, DNA/RNA-based taggants and probes, or PCR products) which when activated are directly or indirectly detectable by Raman spectroscopy. As shown in FIG. 4, the surface modifications may be either heterogeneous or homogeneous, in accordance with an embodiment. The aerosol collection material may interface with an interchangeable or disposable collection trap, accretion well, cup, plate, filter, or impinger. The substrate and collection housing may allow encapsulation to eliminate user contact/contamination with the sampling material and safe transport to supporting analytical laboratories.

The device may also comprise an outlet 250 through which the sampled air is expelled, blown, or otherwise removed from the collection device 200.

According to an embodiment, a probe 260—such as a fiber optic probe—connects a spectrometer (not shown in FIG. 2) to aerosol collector 200 via an attachment mechanism which allows engagement and disengagement for possible dual use of the probe. The probe is situated, for example, perpendicular to the surface of the collection substrate or at an angle less than 90 degrees inside the aerosol collector to allow for frequent (or constant) interrogation and analysis of the substrate's surface with minimal external electromagnetic interferences. According to an embodiment, the probe is designed not to interfere with the efficiency and airflow within the collection device. Interrogation of the collection surface could occur on either face of the collection substrate (i.e. through the material if it is optically possible using the wavelength and power of the probe).

At step 130 of the method depicted in FIG. 1, the sample is analyzed by a spectrometer. According to one embodiment, a Raman spectrometer interrogates the surface of the collection substrate (which contains the aerosolized threats substance) while situated in place in the collection device. According to an embodiment, the Raman spectrometer can be a standard device used in, for example, chemical and material analysis, although the Raman spectrometer used for this application would preferably be a system that is compact and designed for field use. Typically, the Raman spectrometer excites the surface of a sample with a specific laser power and wavelength (such as, for example, 785 nm), and records and compares the electromagnetic spectrum from consequently dispersed by the sample to a library of chemical or biological threats. Other wavelengths for Raman spectroscopy such as 1064 nm and modifications of the spectroscopic technique used to interrogate the collection are possible such as absorption, infrared, and fluorescence spectroscopy. For example, alternative techniques could include laser induced breakdown spectroscopy ("LIBS") or sum frequency generation spectroscopy ("SFG") as well as others.

Either during or after operation of the aerosol collector, a spectrometer (possibly Raman) pulses a laser at the collection substrate, and analyzes the presence of a chemical or biological threat on the substrate's surface. The laser can perform intermittent interrogations throughout the collection period or upon finalization of a defined pre-programmed time. The spectral processing algorithm of the spectrometer identifies the presence of "peaks" or "bands" within the spectrum that represent molecular functional groups inherent to threat chemicals or biologicals. Additional sample analysis may be enhanced by the "processing" of multiple sensor data at the time of any single detection.

At step 140 of the method, the unknown aerosolized biological and/or chemical agent is identified. According to an embodiment, identification occurs by comparing the spectral results obtained from the collected aerosol to a library of pre-programmed or pre-populated biological and/or chemical threat spectra. A match can be determined based on a set signal to noise threshold, predetermined matching algorithm, or set of multi-sensor criteria defined by the combined sensor data. According to an embodiment, a method or system capable of comparing an obtained Raman spectrum to a database of predetermined Raman spectral scattering profiles may require additional components, such as a processor and a communications link or could reside locally on the device in an integrated fashion. The storage device may include system memory, such a read only memory (ROM) and/or random access memory (RAM). The storage device can include any suitable type of physical data storage including, for example, a flash card, solids state or optical hard disk drive, or any other type of storage medium for reading from and writing to. Alternatively, the database could be stored remotely in a virtual state via a cloud-based system. The database of predetermined profiles can be updated with newly acquired spectral profiles either locally or remotely, including on a periodic basis.

According to yet another embodiment, at step 150 of the method, the device or system can comprise one or more elements or components to alert a user to the presence of an aerosol biological and/or chemical threat, if such a threat is detected. For example, an alarm system can be integrated directly into the spectrometer such that it activates an alert—which can be a local or remote visual alert or in the form of a sound, text, call, or other alert or notification—when an identified biological and/or chemical threat is found in a sample. Alternatively, the alarm component or system can be integrated into a controller or processor in communication with the Raman spectrometer and/or aerosol collector. Communication can be wired or wireless, and the processor/controller can be local or remote. Accordingly, the system can comprise a pre-programmed or pre-populated database that contains biological and/or chemical threat profile and information relevant to the user such as physical/chemical/biological properties, hazards such as toxicological profiles, expected environmental transport characteristics and decontamination methods. Therefore, if an identification occurs, the user will be provided actionable information appropriate for a first responder, emergency management officials, or other decision makers to protect those in danger of the chemical or biological threat.

The method or system may also comprise a user interface that a user can employ to enter commands and information, or receive commands and information (including data and controls regarding the spectrometer or aerosol collector), and can comprise a user terminal such as a smart TV module, a personal computer, or a mobile device, as well as an input device, such as a keyboard and pointing device (e.g., a mouse), touchscreen tablet, smartphone, microphone for voice activation, or a video camera. These and other input devices can be connected, through an appropriate interface, to the network (e.g., the Internet) or a system bus, and to one or more processors. In addition (or instead of) the monitor, the user terminal may include other (peripheral) output devices (not shown), such as speakers and printers for example. In some cases, output device can include a component for providing one or more forms of output such as, a visual output, a haptic output, or an audio output.

Given that Raman spectroscopy is non-destructive, at step 160 of the method, the chemical threat aerosol collected onto the removable collection substrate or sample cup 240 allows for downstream analysis of the aerosol, including, for example, confirmatory analysis of the detected or undetected chemical and/or biological threat aerosol by extraction. For example, following an alarm noting a possible release of a chemical threat aerosol, the contaminated collection substrate from the aerosol collector can be processed directly in the field or at a supporting laboratory. Once received by the supporting laboratory, the sample can be processed and analyzed by a variety of laboratory grade analytical instruments, which allow for more precise, sensitive, and comprehensive characterization of the sample.

Figure 3:
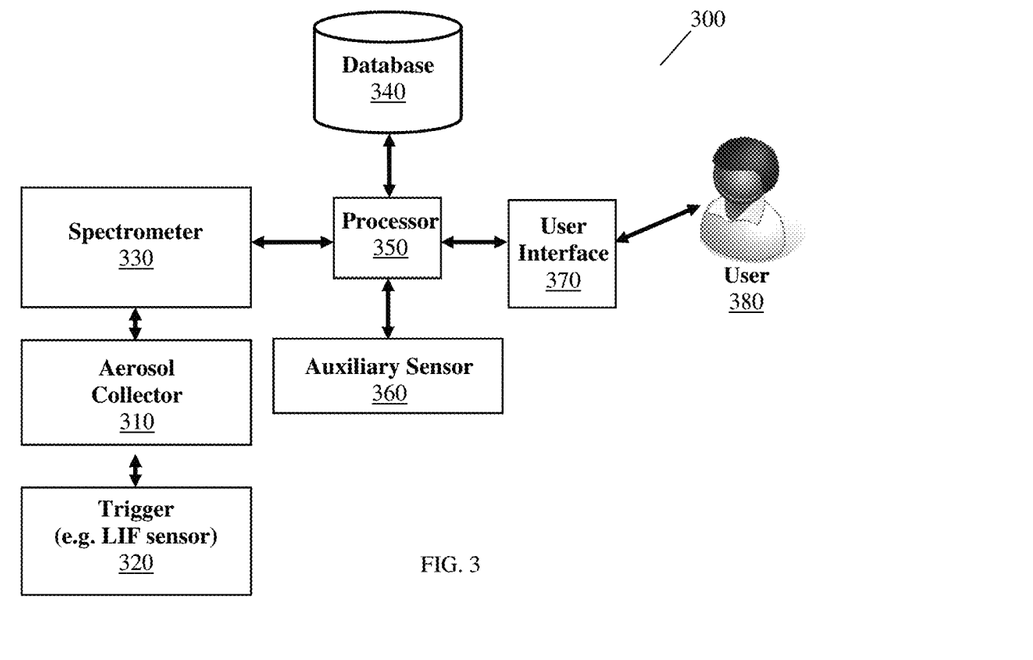
FIG. 3 is a schematic representation of a system adapted to collect and detect a biological and/or chemical agent or aerosol according to one embodiment.

Referring to FIG. 3, in accordance with an embodiment, is a system 300 for collecting and identifying an aerosolized agent. The system includes an aerosol collector or dry particulate sampler device which collects the aerosol. The aerosol collector can be any of the aerosol collectors described or otherwise envisioned herein. For example, the aerosol collector can include a fan, blower, or pump generating airflow of a specific volumetric flow rate directed at or through an aerosol collection substrate situated within a collection chamber. The aerosol collector can also include an integrated trigger 320 to initiate sample collection upon detection of a chemical and biological threat. This trigger system can include algorithms to differentiate between biological and chemical threats. Such a trigger may be a modified UV light induced fluorescence or Raman Scattering detector using either a laser, light emitting diode, or other appropriate excitation sources. Many other types of triggers are also possible.

According to an embodiment, a probe—such as a fiber optic probe—connects a spectrometer 330 to aerosol collector via an attachment mechanism which allows engagement and disengagement for possible dual use of the probe. The probe is situated, for example, near the surface of the collection substrate inside the aerosol collector to allow for frequent (or constant) interrogation and analysis of the substrate's surface with minimal external electromagnetic interferences. According to one embodiment, a Raman spectrometer 330 interrogates the surface of the collection substrate (which contains the aerosolized threats substance) while situated in place in the collection device. According to an embodiment, the Raman spectrometer can be a standard device used in, for example, chemical and material analysis, although the Raman spectrometer used for this application would preferably be a system that is compact and designed for field use. Typically, the Raman spectrometer excites the surface of a sample with a specific laser power and wavelength (such as, for example, 785 nm), and records and compares the electromagnetic spectrum from consequently dispersed by the sample to a library of chemical or biological threats. Other wavelengths for Raman spectroscopy such as 1064 nm and modifications of the spectroscopic technique used to interrogate the collection are possible such as absorption, infrared, and fluorescence spectroscopy. For example, alternative techniques could include laser induced breakdown spectroscopy or sum frequency generation spectroscopy as well as others.

According to an embodiment, system 300 includes a database 340 and a processor 350, utilized to identify the unknown aerosolized biological and/or chemical agent. Database 340 and processor 350 may be separate components of the same device, for example, or may be components of two or more separate devices. According to an embodiment, identification occurs by comparing the spectral results obtained from the collected aerosol to a library of pre-programmed or pre-populated biological and/or chemical threat spectra, which is stored in database 340. A match can be determined based on a set signal to noise threshold, predetermined matching algorithm, or set of multi-sensor criteria defined by the combined sensor data. According to an embodiment, a method or system capable of comparing an obtained Raman spectrum to a database of predetermined Raman spectral scattering profiles may require additional components, such as a processor and a communications link or could reside locally on the device in an integrated fashion. Database 340 can be any suitable type of physical data storage including, for example, a flash card, solids state or optical hard disk drive, or any other type of storage medium for reading from and writing to. Alternatively, the database could be stored remotely in a virtual state via a cloud-based system. The database of predetermined profiles can be updated with newly acquired spectral profiles either locally or remotely, including on a periodic basis.

According to yet another embodiment, system 300 includes a user interface 370 configured to alert a user 380 to the presence, or absence, of an aerosolized agent. User 380 can engage the interface 370 to provide commands and information, or receive commands and information (including data and controls regarding the spectrometer or aerosol collector). According to an embodiment, user interface 370 can include a user terminal such as a smart TV module, a personal computer, or a mobile device, as well as an input device, such as a keyboard and pointing device (e.g., a mouse), touchscreen tablet, smartphone, microphone for voice activation, or a video camera. These and other input devices can be connected, through an appropriate interface, to a network (e.g., the Internet) or a system bus, and to one or more processors. In addition (or instead of) the monitor, the user terminal may include other (peripheral) output devices (not shown), such as speakers and printers for example. In some cases, output device can include a component for providing one or more forms of output such as, a visual output, a haptic output, or an audio output.

According to an embodiment, user interface 370 can include an alerting mechanism to alert a user to the presence of an aerosol biological and/or chemical threat, if such a threat is detected. For example, an alarm system can be integrated directly into the spectrometer such that it activates an alert—which can be a local or remote visual alert or in the form of a sound, text, call, or other alert or notification—when an identified biological and/or chemical threat is found in a sample. Alternatively, the alarm component or system can be integrated into a controller or processor in communication with the Raman spectrometer and/or aerosol collector. Communication can be wired or wireless, and the processor/controller can be local or remote. Accordingly, the system can comprise a pre-programmed or pre-populated database that contains biological and/or chemical threat profile and information relevant to the user such as physical/chemical/biological properties, hazards such as toxicological profiles, expected environmental transport characteristics and decontamination methods. Therefore, if an identification occurs, the user will be provided actionable information appropriate for a first responder, emergency management officials, or other decision makers to protect those in danger of the chemical or biological threat.

Figure 6:
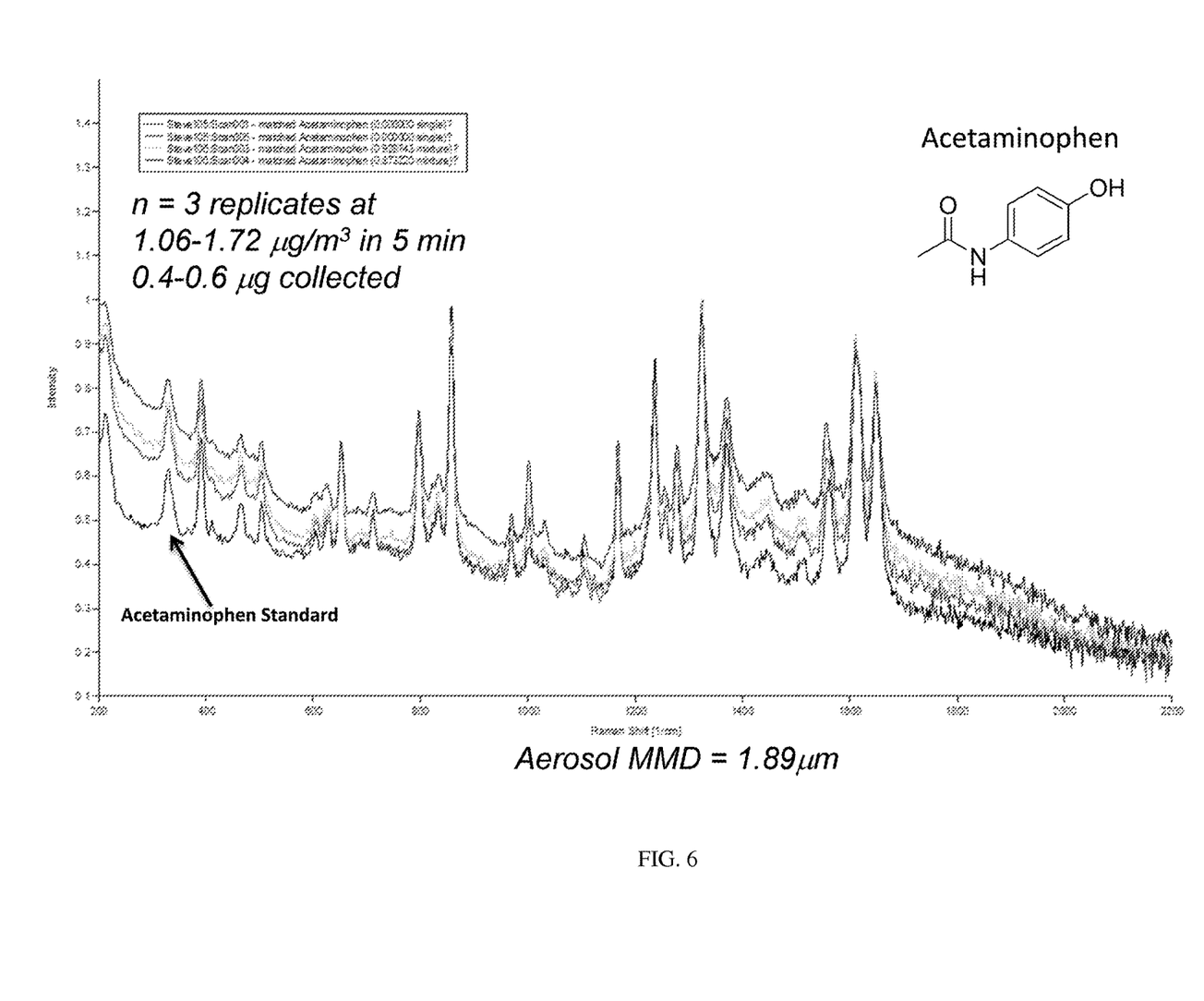
FIG. 6 is a representative Raman spectral overlay in triplicate of aerosolized acetaminophen powder at a specified detection limit compared against a standard bulk analysis.
Figure 7:
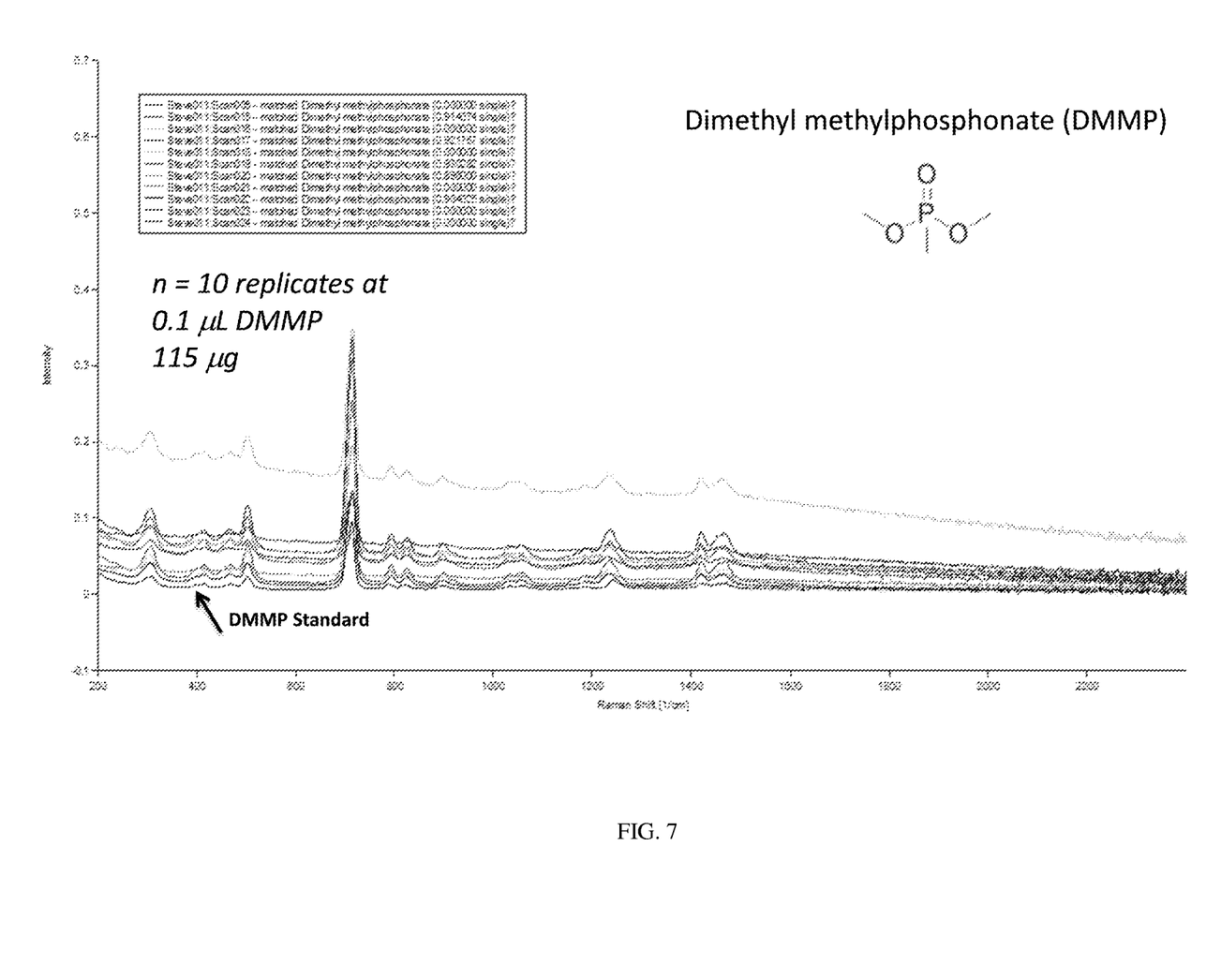
FIG. 7 is a representative Raman spectral overlay of (n=10) of 0.1 μL of liquid chemical simulant dimethyl methylphosphonate (DMMP) on a collection substrate compared against a standard bulk analysis.
Figure 8:
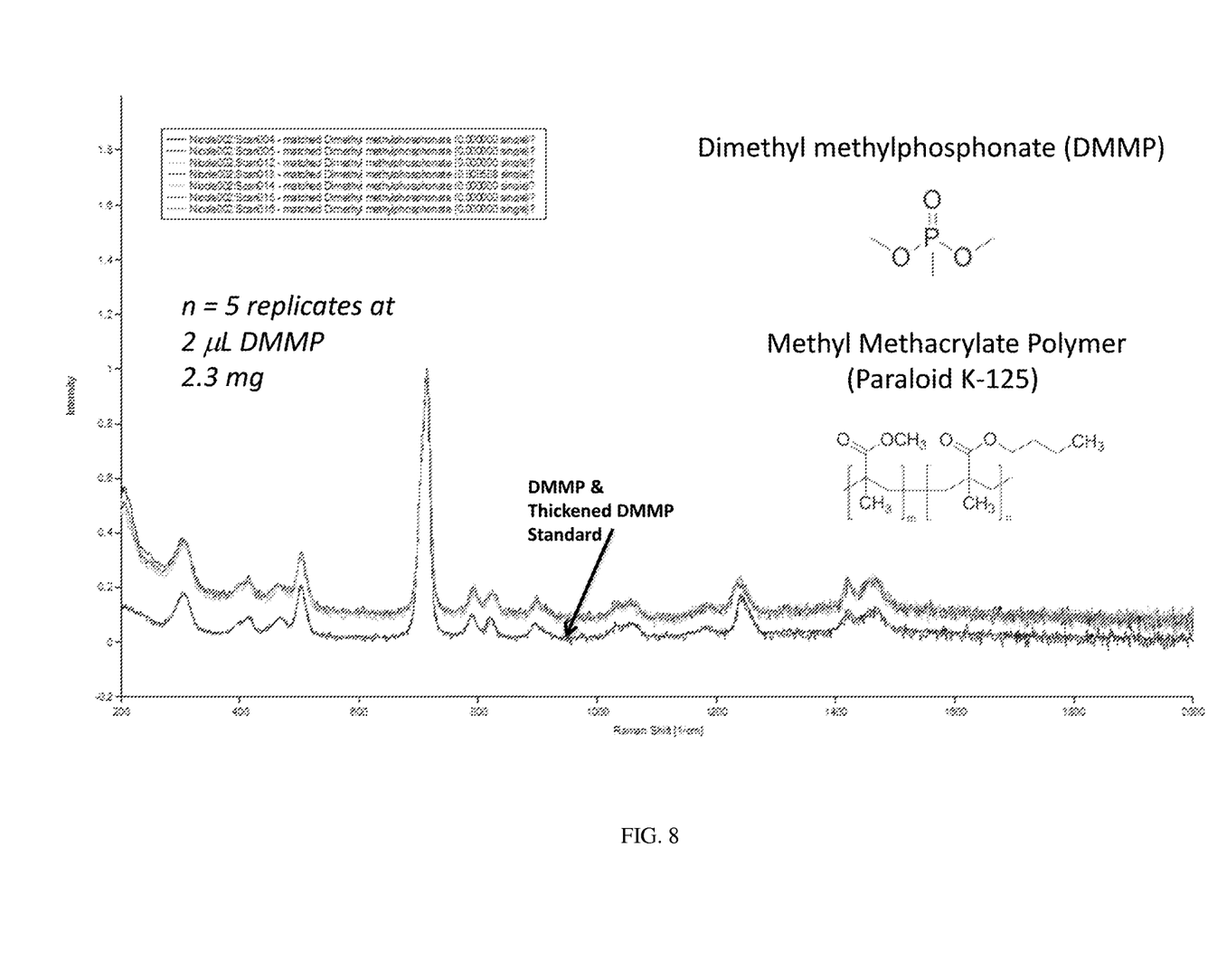
FIG. 8 is a representative Raman spectral overlay of (n=5) of 2 μL of liquid chemical simulant dimethyl methylphosphonate (DMMP) thickened with Paraloid K-125 on collection substrate compared against a standard bulk analysis.
Figure 9:
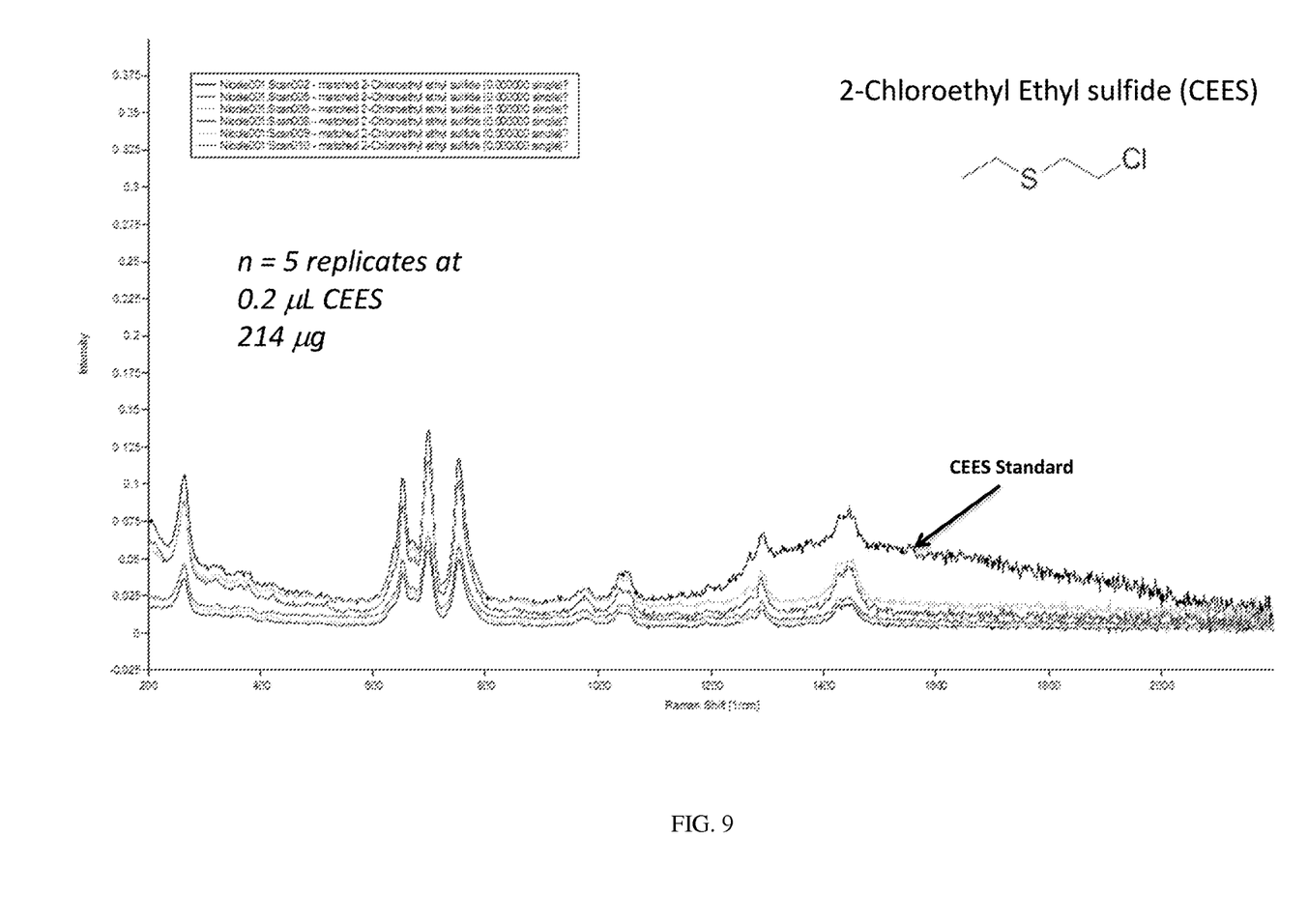
FIG. 9 is a representative Raman spectral overlay of (n=5) of 0.2 μL of liquid chemical simulant 2-chloroethyl ethyl sulfide (CEES) on collection substrate compared against a standard bulk analysis.
Figure 10:
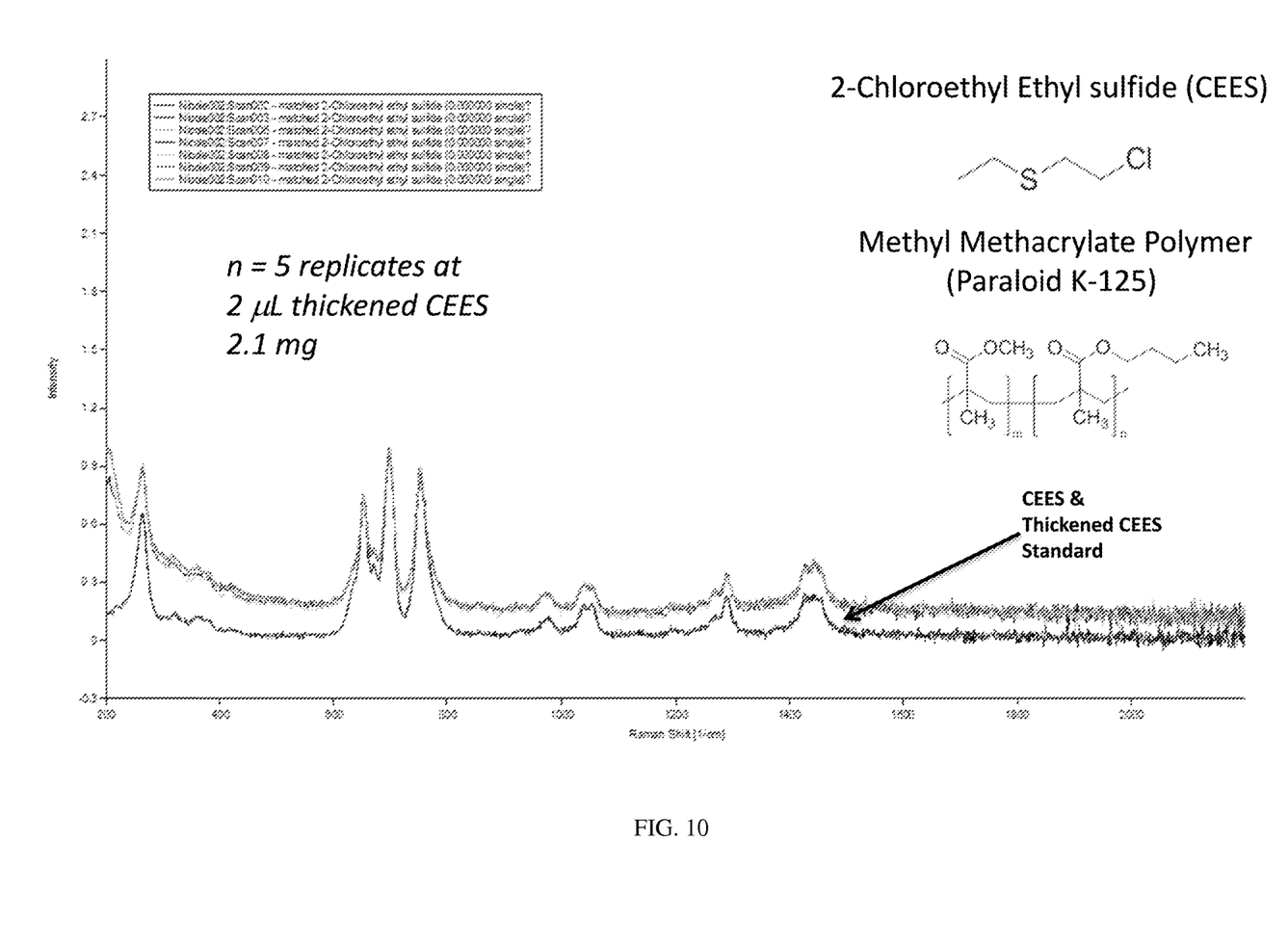
FIG. 10 is a representative Raman spectral overlay of (n=5) of 2 μL of liquid chemical simulant 2-chloroethyl ethyl sulfide (CEES) thickened with Paraloid K-125 on collection substrate compared against a standard bulk analysis.
Figure 11:
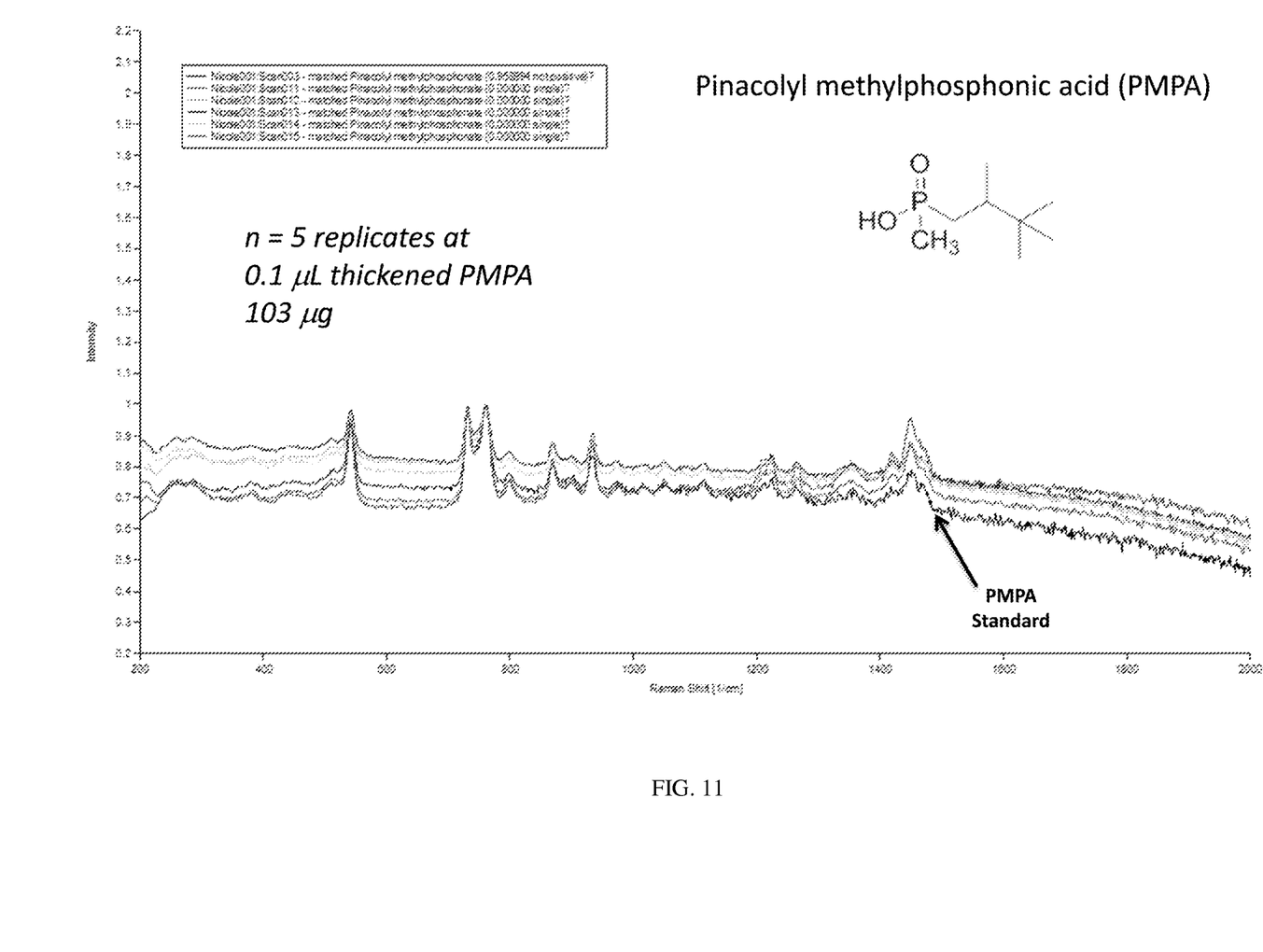
FIG. 11 is a representative Raman spectral overlay of (n=5) of 0.1 μL of liquid chemical simulant pinacolyl methylphosphonic acid (PMPA) on collection substrate compared against bulk analysis.

Referenced laboratory testing on the system, method, and device described is shown in FIG. 5-11. A modified LIF detector was tested to act as an aerosol trigger used to initiate the aerosol collector/identifier device and validate the system approach to the detection platform presented herein. The fluorescence spectrum of a chemical challenge (acetaminophen) was collected as a reference standard as shown in the top left of FIG. 5, and compared to an authentic aerosol chamber challenge of acetaminophen collected by the LIF detector as shown in the top right of FIG. 5. Acetaminophen was used as a general simulant of solid aerosol material. The modified LIF detector recognized the characteristic fluorescence and/or Raman scattering signature with only algorithm changes and can be programmed to that of chemical and biological threat materials that could trigger a subsequent collection and identification using spectroscopic techniques. Laboratory testing of a prototype device described herein resulted in validation of a device that can collect, detect, and identify solid and liquid chemical challenges via Raman spectroscopy. The resulting Raman spectra of triplicate aerosol challenges of acetaminophen powder with a median mass diameter (MMD) of 1.89 µm are shown in FIG. 6. Testing of the acetaminophen powder resulted in a limit of detection (LOD) around 1-2 µg/m$^3$ following a 5 minute sample collection period. Liquid simulant testing shown in FIG. 7-11 on the collection substrate described herein resulted in confirmation that fluorescence background reduction and signal enhancement is sufficient to see rapid detection of droplets ranging from 0.1 µL neat simulant and 2 µL of thickened simulant.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The above-described embodiments of the described subject matter can be implemented in any of numerous ways. For example, some embodiments may be implemented using hardware, software or a combination thereof. When any aspect of an embodiment is implemented at least in part in software, the software code can be executed on any suitable processor or collection of processors, whether provided in a single device or computer or distributed among multiple devices/computers.

What is claimed is:

1. A method for identifying an aerosolized agent, the method comprising the steps of:
   providing a sample, the sample potentially containing an aerosolized agent;
   concentrating the sample with an aerosol collector, the aerosol collector comprising a collection chamber configured to direct the sample to a collection substrate configured to limit interference by background fluorescence;
   analyzing the concentrated sample on the collection substrate using spectroscopy to produce an aerosolized agent analysis output;
   comparing the analysis output to a database comprising a plurality of known agent analysis outputs;
   identifying the aerosolized agent based on said comparing step; and
   alerting a user to the presence of an aerosolized agent in said sample.

2. The method of claim 1, wherein said agent is a biological agent.

3. The method of claim 1, wherein said agent is a chemical agent.

4. The method of claim 1, further comprising the step of transferring the collected sample to supporting laboratory for further analysis.

5. The method of claim 1, further comprising the step of triggering the concentration of the sample by the aerosol collector.

6. The method of claim 5, further comprising the step of analyzing the concentrated sample using a second sensor.

7. A device configured to concentrate an aerosolized agent, the device comprising:
   an air movement device configured to force air comprising the aerosol into an inlet, wherein said air may comprise the aerosolized agent;
   a collection chamber configured to direct the air to a collection substrate configured to limit interference by background fluorescence;
   a spectrometer probe positioned to analyze a surface of the collection substrate.

8. The device of claim 7, wherein said agent is a biological agent.

9. The device of claim 7, wherein said agent is a chemical agent.

10. The device of claim 7, wherein said air movement device is a fan.

11. The device of claim 7, wherein said collection substrate is replaceable.

12. A system configured to identify an aerosolized agent, the system comprising:
    an aerosol collector configured to concentrate an aerosolized agent, the aerosol collector comprising a collection chamber configured to direct the sample to a collection substrate configured to limit interference by background fluorescence;
    a spectrometer in communication with the aerosol collector, the spectrometer configured to analyze the concentrated aerosolized agent;
    a database of biological and chemical agents; and
    a processor in communication with the spectrometer and the database, the processor configured to compare the results of the analysis to the database of known agents, and further configured to identify the concentrated aerosolized agent based on the comparison.

13. The system of claim 12, wherein said agent is a biological agent.

14. The system of claim 12, wherein said agent is a chemical agent.

15. The system of claim 12, further comprising a trigger for initiating aerosol collection by the aerosol collector.

16. The system of claim 15, further comprising an auxiliary sensor in communication with the trigger.

17. The system of claim 12, further comprising a user interface.

\* \* \* \* \*